United States Patent [19]

Bruylants et al.

[11] 4,145,301

[45] Mar. 20, 1979

[54] PROCESS FOR PREPARING MAGNETIC OXIDES

[75] Inventors: Philippe M. Bruylants, Winksele, Belgium; José J. Fripiat, Orleans, France; Luc W. Rodrigue, Louvain, Belgium; Georges M. Poncelet, Beauvechain, Belgium; Antonin A. Munaut, Louvain-la-Neuve, Belgium

[73] Assignee: Unibra Societe Anonyme, Brussels, Belgium

[21] Appl. No.: 737,826

[22] Filed: Nov. 1, 1976

[30] Foreign Application Priority Data

Oct. 31, 1975 [AT] Austria ............................... 8298/75

[51] Int. Cl.² .......................................... C01G 49/06
[52] U.S. Cl. .............................. 252/62.56; 252/62.57; 252/62.62; 252/62.63; 423/633; 423/634; 423/594
[58] Field of Search ............... 252/62.56, 62.62, 633, 252/62.57, 62.63; 423/634, 594

[56] References Cited

U.S. PATENT DOCUMENTS

| | | | |
|---|---|---|---|
| 3,573,980 | 4/1971 | Haller et al. | 252/62.56 X |
| 3,928,709 | 12/1975 | Audran et al. | 252/62.56 X |
| 3,994,819 | 11/1976 | Mollard et al. | 252/62.56 X |

FOREIGN PATENT DOCUMENTS

| | | | |
|---|---|---|---|
| 2235383 | 2/1973 | Fed. Rep. of Germany | 252/62.56 |
| 2352440 | 4/1975 | Fed. Rep. of Germany | 423/634 |

*Primary Examiner*—Jack Cooper
*Attorney, Agent, or Firm*—Sughrue, Rothwell, Mion, Zinn and Macpeak

[57] ABSTRACT

This invention relates to a process for the preparation of magnetic oxides and possibly of at least one other metal. It relates also to new products consisting in mono- and polymetal magnetic oxides.

According to the invention a glycerin complex of iron and possibly at least one other metal is first prepared and the complex is decomposed into a mono- or polymetal magnetic oxide by hydrolysis or pyrolysis, the possibly decomposed glycerin complex being subjected to a thermal treatment, such as annealing or pyrolysis in an atmosphere of an inert gas, such as nitrogen.

The invention relates to magnetic oxides containing 0.2 to 3% by weight of carbon, said oxides preferably containing cobalt and possibly a rare earth element such as yttrium or europium.

11 Claims, No Drawings

PROCESS FOR PREPARING MAGNETIC OXIDES

FIELDS OF THE INVENTION

This invention relates to a process for the preparation of magnetic oxides of iron and possibly of at least one other metal. It relates also to new products consisting in mono- and polymetal magnetic oxides.

The term "polymetal magnetic oxides", as used herein, relates to mixed magnetic oxides containing iron and at least one other metal, whereas the term "monometal magnetic oxides" relates to magnetic oxides containing only iron.

PRIOR ART

It is known to prepare magnetic iron oxides by a process in which a complex of glycerin and iron is first prepared by reacting an iron (II) compound with glycerin and the obtained complex is decomposed by hydrolysis or pyrolysis.

In this known process, the iron compound is dispersed, at room temperature, into an excess of anhydrous glycerin and the reaction mixture is progressively heated up to a temperature comprised between about 110° and 290° C., preferably between about 160° and 290° C., while stirring, for maintaining the solid in dispersed state, during 2 to 20 hours. After cooling of the reaction medium, the excess of glycerin is removed from the crystalline precipitate of glycerin complex by washing it first with distilled water and then with an organic solvent miscible with water and with glycerol. The so obtained crystalline product is finally dried, for example at a temperature of about 70° C.

The so obtained glycerin complex or glycerolate is then decomposed in magnetic oxide by hydrolysis in boiling water or by pyrolysis in the presence of air.

This known process gives crystals of magnetic iron oxides having a homogeneous size of about 250 angströms.

It is known, on the other hand, that the market of the magnetic memories is presently dominated by iron oxides ($\gamma$—$Fe_2O_3$) sometimes doped with cobalt, and by chromium dioxide $CrO_2$. The latter oxide has interesting magnetic properties, but the preparation of this compound is difficult and its magnetic properties are quickly altered at the temperatures (about 70° C. or more) to which it is subjected in current practice. Moreover, the chromium oxide injures the recording heads of the recording apparatuses and causes the appearance of a ground noise during the recording. The iron oxide ($\gamma$—$Fe_2O_3$) does not have the same performances as the chromium dioxide for the sound recordal, but does not have the drawbacks of said chromium dioxide.

For several years, it has thus been attempted to improve the performances of $\gamma$—$Fe_2O_3$ by replacing the iron atoms by other metal cations. In the field of magnetic recording and memories, it has quickly been found that cobalt has uncommon properties. Its high magnetocrystalline anisotropy allows the preparation of iron oxides doped with cobalt, having remarkable properties. However, when more than 10% of cobalt is used, the magnetocrystalline anisotropy due to the cobalt no longer allows the use of the $\gamma$—$Fe_2O_3$ doped with cobalt in magnetic tapes. However, with such cobalt content, the doped iron oxides may be used in drums, records and tapes of computers and video apparatuses. Furthermore, high percentages of cobalt, for example from 20 to 50%, allow the manufacture of permanent magnets which are useful in many fields.

DESCRIPTION OF THE INVENTION

The present invention relates to improvements to the known processes for preparing magnetic oxides from glycerin complexes or glycerolates. It concerns also magnetic oxides having new properties which make them very useful in the field of recording conventional magnetic tapes and similar applications.

The process according to this invention is mainly characterized by the fact that the glycerin complex decomposed into a mono- or polymetal magnetic oxide is subjected to the thermal treatment in an atmosphere of at least one inert gas, such as nitrogen, carbon dioxide, helium, hydrogen or water vapor.

In a first embodiment of the process according to this invention, the glycerin complex when decomposed into an oxide by hydrolysis, is subjected to an annealing thermal treatment at a temperature of about 300° to 500° C., preferably of about 350° C., in an atmosphere of an inert gas. Grains of magnetic oxide are obtained. The size of the granular crystals of mono- or polymetal magnetic oxides obtained according to this embodiment is substantially larger than that of the crystals obtained by the known processes.

The annealing treatment of the glycerin complexes decomposed by hydrolysis, in a nitrogen atmosphere, gives crystals having a size of about 500 angströms. This increase of the size of the oxide grains is quite beneficial for the use of said oxides.

Moreover, the crystals of magnetic oxides obtained according to the first embodiment of the process of this invention have an ordered structure, as shown by the presence of intense and narrow peaks in the X-ray diffraction spectra thereof, whereas the conventional magnetic oxides obtained by the known processes do not have such an ordered structure.

According to a second embodiment of the process according to this invention, the glycerin complex is subjected immediately to a pyrolysis at a temperature of about 300° to 500° C., preferably of about 350° C., in an atmosphere of an inert gas. Crystals having the shape of laths with numerous small holes (monoporous morphology) are thus obtained.

The magnetic oxides, particularly the polymetal magnetic oxides obtained by the process according to the invention have a homogeneous structure and have a carbon content of about 0 to 3% by weight, said carbon content being generally of about 1%.

The magnetic iron oxides obtained by pyrolysing glycerin complexes under air consist of a mixture of $\gamma$—$Fe_2O_3$ and $\alpha$—$Fe_2O_3$. In said mixture, the sole phase which has magnetic properties, due to the fact that it is ferrimagnetic, is the $\gamma$—$Fe_2O_3$ phase, whereas the second phase is antiferromagnetic and has therefore a non magnetic behaviour. It has been found that, when the pyrolysis takes place under an atmosphere of an inert gas, such as nitrogen, instead of under an atmosphere of air as in the known processes, the content of ferrimagnetic phase ($\gamma$—$Fe_2O_3$) increases whereas the content of antiferromagnetic phase ($\alpha$—$Fe_2O_3$) decreases, so as to improve the magnetic properties of the oxide, while avoiding the formation of hematite.

It is possible to obtain, by the process according to this invention, polymetal magnetic oxides containing, besides iron, at least one other metal selected among nickel, chromium, manganese, cobalt, zinc, strontium, yttrium, ruthenium, rhodium, barium, lanthanum, cerium, praseodymium, neodymium, promethium, samarium, europium, gadolinium, terbium, dysprosium, holmium, erbium, thulium, ytterbium, tungsten and lead, from a mixed glycerin complex having a homogeneous composition and obtained by reaction of glycerin with a mixture of selected metal compounds.

While the known processes for the preparation of magnetic oxides by decomposition of glycerin compounds only relate to the preparation of monometal magnetic oxides, it has been found that it is possible to obtain polymetal magnetic oxides by preparing first mixed glycerin complexes having a particularly homogeneous composition, by reacting glycerin with a mixture of an iron salt and of a salt of at least one other metal, preferably a nickel, cobalt, chromium, manganese or zinc salt, the process according to this invention allowing the formation from said mixed glycerin complexes of mixed magnetic oxides in which said other metal is homogeneously distributed in the crystals. It has been found that, among the various other metals useful for obtaining mixed magnetic oxides, cobalt is particularly interesting.

The mixed iron and cobalt glycerin complexes are decomposed into mixed magnetic oxides by hydrolysis, preferably in a Soxhlet apparatus, followed by a thermal annealing under nitrogen. It has first been found that the thermal annealing of the mixed oxides obtained by hydrolysis increases very substantially the magnetic properties thereof. The thermal annealing has also a favorable influence on the purity of the magnetic oxides and on the size of the oxide grains, so that increases of the coereitive fields of sometimes more than 100% can be obtained. Moreover, the presence of cobalt improves substantially the magnetic properties. In this respect, in the oxides obtained by hydrolysis followed by a thermal annealing there is a linear relation between the percentage of cobalt and the coereitive field. The magnetocrystalline anisotropy, due to the cobalt, thus allows the use of non-acicular oxide particles. When the percentage of cobalt is high (for example 10%), the oxides have the behaviour of hard ferrites and may be used for the manufacture of magnets.

It has been found that good magnetic properties may be obtained with weight percentages of at least 2 to 2.5% of cobalt in the mixed magnetic oxides. When the proportion of cobalt is decreased, the magnetic properties are impaired. This shows that there is a limit of about 2.5% of cobalt, below which the presence appearance of the demagnetizing field in the non-acicular mixed oxide particles detrimentally affects the favourable effect of cobalt.

However, when it is desired to obtain with mixed iron and cobalt magnetic oxides values of the coereitive field which are suitable for the magnetic recording, without changing the remanent and saturation inductions, it is possible, according to the present invention, to dope said mixed oxides of iron and cobalt containing less than 2% of the latter metal, with a rare earth element. For that purpose, a mixed glycerin complex is first prepared from salts of iron, cobalt and at least one rare earth element and said glycerin complex is decomposed by the process according to this invention. Among the rare earths which may be used, the following may be cited: yttrium, lanthanum, cerium, praseodymium, neodymium, samarium, europium, gadolinium, terbium, dysprosium, holmium, erbium, thulium, ytterbium and thorium. In this series, yttrium, europium, samarium, terbium and ytterbium are particularly interesting. It has been found that the iron-cobalt-yttrium mixed oxides, when annealed in accordance with this invention, have interesting properties. Thus, when increasing proportions of yttrium are present in the mixed oxides, the values of the coereitive field decrease, whereas the remanent induction remains practically unchanged. Due to this unexpected property, it is possible to change at will the behaviour of the magnetic oxides. Generally speaking it may be said that the magnetically too hard character of the cobalt is reduced by the addition of small amounts of a rare earth element.

As already pointed out, the magnetic oxides obtained by the process according to this invention contain carbon. The presence of carbon at a content of about 1% is particularly interesting when the magnetic oxides are used, namely for the manufacture of magnetic tapes. Tests of manufacture of magnetic tapes have shown the considerable advantage of the presence of carbon, in comparison with the use of the common magnetic oxides which do not contain carbon. This advantage seems to result from the affinity of said carbon containing oxides with the resin used in the magnetic tapes. The homogeneity of the distribution of the magnetic oxide in the resin as well as the use easiness of said oxide are also significantly improved, the particles of the carbon containing magnetic oxide having a better dispersibility in the resin. All these features substantially improve the quality of a magnetic tape.

EXAMPLES

The following examples illustrate the invention. In these examples, the magnetic properties have been measured at room temperature by means of a vibrating sample magnetometer PAR Föner. The coereitive fields (Hc) are expressed in oersted and the remanent (Br) and saturation (Bs) inductions ingauss. The measures have been made in a field of 10 kOe. A Hall probe has been used for measuring the field values. The saturation specific magnetization ($\sigma s$) has been measured in a SERMAG sigmameter, in which the field in the air gap had a value of 13 kOe. The factor $\sigma s$ is expressed in Oe. cm3/g.

EXAMPLE 1

A. 20 g of iron (II) oxalate are dispersed in 300 ml of anhydrous glycerin. The dispersion is slowly heated, while stirring, during 6 hours, until a temperature of 240° C. is reached. After cooling the precipitate is washed and separated from the excess of glycerin by means of distilled water. After final washing with methanol, the product is dried in a drier at 70° C. After 5 hours, the product is crushed in a mortar. The weight of the obtained glycerin complex is 15 g.

Following table I gives the X-ray difraction data of this glycerin complex, whereas following table II gives the position of the infrared absorption bands of said complex, as well as the relative intensities of said bands. Table III gives the results of the chemical analysis of the glycerin complex.

TABLE I

| X-RAYS DIFFRACTION | |
|---|---|
| $\delta$ (A) | Relative intensity |
| 8.112 | 100 |
| 7.46 | 45 |
| 5.34 | 22 |
| 4.97 | 34 |
| 4.35 | 76 |

TABLE I-continued

| X-RAYS DIFFRACTION | |
|---|---|
| δ (A) | Relative intensity |
| 4.22 | 45 |
| 4.05 | 23 |
| 3.71 | 18 |
| 3.63 | 3 |
| 3.29 | 21 |
| 3.11 | 33 |
| 2.89 | 18 |
| 2.82 | 34 |

TABLE II

| INFRARED SPECTROSCOPY | | |
|---|---|---|
| Y (cm$^{-1}$) | Relative intensity % | Attribution residual OH |
| 3455 | 19 | |
| 2935 | 23 | CH$_2$ and CH stretching |
| 2900 | 39 | |
| 2853 | 61 | |
| 1473 | 6 | |
| 1460 | 7 | |
| 1447 | 12 | |
| 1346 | 15 | CH$_2$deformation |
| 1325 | 16 | |
| 1318 | 15 | |
| 1307 | 12 | |
| 1299 | 12 | |
| 1255 | 6 | |
| 1232 | 6 | |
| 1227 | 6 | |
| 1212 | 3 | |
| 1133 | 83 | |
| 1118 | 82 | |
| 1093 | 45 | |
| 1090 | 41 | |
| 1063 | 100 | C—O stretching |
| 1051 | 77 | |
| 1021 | 70 | |
| 1008 | 52 | |
| 967 | 34 | |
| 928 | 3 | |
| 906 | 13 | CH$_2$ deformation |
| 823 | 89 | |
| 804 | 61 | |
| 779 | 36 | |
| 711 | 4 | |

TABLE III

| CHEMICAL ANALYSIS | | | |
|---|---|---|---|
| % C | % H | % O | % Fe |
| 22.47 | 3.31 | 30.53 | 43.6 |

The glycerin complex identified in tables I, II and III is then decomposed into a magnetic oxide by hydrolysis, as follows:

B. 3g of the glycerin complex are dispersed in 1800 ml of distilled water. The obtained mixture is heated at the boiling temperature during 2 hours and the so obtained solution is centrifuged. The iron oxides are then dried during 12 hours at 110° C. 1.8 g of magnetic iron oxide are obtained.

The X-rays show peaks identical to those of magnetic iron oxide having a spinel structure. The iron oxide has also the granular morphology which is typical of the used method. It has a coercitive field of 104 Oe and a σ s of 58.2.

C. The iron oxide prepared as described in this example 1, B is subjected to a thermal treatment at 300° C. during 1 hour, under a stream of nitrogen having a flow rate of 0.1 liter/minute.

The magnetic features of the oxide so subjected to a thermal annealing are as follows: Hc = 225, Oe and σ s = 72.7.

Compared to the oxide obtained as described in example 1B, the annealed oxide has clearly improved magnetic features. When the infrared spectra of the two oxides are compared, it appears that the annealed oxide no longer shows the absorption peaks which are characteristic of the presence of water, this feature explaining partly the increase of σ s.

Following table IV shows the magnetic data of the oxide prepared as described in example 1B and in example 1C.

TABLE IV

| Example | Hc | Br | Bs | Σ s |
|---|---|---|---|---|
| 1B | 104 | 1000 | 2700 | 58.2 |
| 1C | 225 | 1232 | 3500 | 72.7 |

This table shows that due to the thermal annealing treatment according to this invention (example 1C), the magnetic properties of the oxide are substantially improved.

EXAMPLE 2

A. A glycerin complex is prepared in the manner described in example 1A.

When this glycerin complex is pyrolyzed in the presence of air instead of an inert gas, a mixture of magnetic oxides and hematite is obtained, said mixture having a coereitive field of 73 and a σ s of 50.

B. The glycerin complex obtained as described in example 1A is decomposed under a stream of nitrogen at a temperature of 350° C. during 1 hour. After cooling, the oxide is annealed under air at 250° C. during 1 hour.

Following table V shows that the magnetic properties of the oxide obtained in accordance with the present invention (example 2B) are substantially better than those of the oxide obtained by pyrolyzing the glycerin complex in the presence of air (example 2A).

TABLE V

| Example | Hc | Br | Bs | σ s |
|---|---|---|---|---|
| 2A | 73 | 655 | 1840 | 50 |
| 2B | 98 | 1050 | 2700 | 60 |

EXAMPLE 3

A. 20 g of iron (II) oxalate and 1.7029 g of cobalt nitrate are mixed, said mixture containing 5% by weight of cobalt.

The mixture is dispersed into 300 ml of anhydrous glycerin and the dispersion is progressively heated up to 230° C., while stirring, and maintained at this temperature during 6 hours. The cooled precipitate is washed first with water and then with methanol. After drying, it is crushed and weighed. 15 g of a glycerin complex having infrared and X-ray spectra similar to those of the glycerin complex obtained in example 1A are obtained.

3.39 g of said complex are dispersed in 1800 ml of distilled water and the obtained mixture is maintained at boiling temperature during 2 hours. After centrifugation of the solution and drying of the product during 12 hours at 110° C., 2.02 g of an oxide are obtained. This oxide has a Oe of 675 and a σ s of 61.

B. The oxide obtained as described in example 3A is subjected to a thermal annealing during 1 hour at 300° C. under a stream of nitrogen of 0.5 liter/minute. The magnetic data of the annealed oxide are as follows: Hc = 1050 Oe and σ s = 74. The X-rays spectrum show a better ordered structure than that of the oxide obtained in example 3A.

C. The glycerin complex obtained in example 3A is hydrolysed in a Soxhlet apparatus during 24 hours. The obtained magnetic oxide is dried during 12 hours at 110° C. The X-rays spectrum is characteristic of a magnetic oxide having the structure of a spinel; Hc = 850 Oe and $\sigma$ s = 70.

D. The hydrolysed oxide obtained in example 3C is thermally annealed during 1 hour at 350° C. under a stream of nitrogen of 0.5 liter/minute. The X-rays diagrams show a well ordered spinel structure and the magnetic data are as follows: Hc = 1150 Oe and $\sigma$ s = 75.

Table VI shows the magnetic data and the carbon and cobalt contents of the oxides obtained in paragraphs A, B, C and D of example 3.

TABLE VI

| Example | Hc | $\sigma$ s | % C | % Co |
|---|---|---|---|---|
| 3A | 675 | 68 | 0.6 | 5.25 |
| 3B | 1050 | 74 | 0.43 | 5.23 |
| 3C | 825 | 70 | 0.36 | 4.31 |
| 3D | 1170 | 75 | 0.21 | 4.3 |

This table shows that, when operating under the conditions of this invention (examples 3B and 3D), the magnetic properties of the mixed iron and cobalt oxides are clearly better than those of the oxides obtained according to the prior art (example 3A). Moreover, it appears that an hydrolysis by means of a Soxhlet apparatus of the mixed complex (example 3C) improves also the mixed magnetic oxide.

EXAMPLE 4

A. 5g of iron (II) oxalate and 60 mg of europium nitrate are mixed. The mixture contains 0.5% by weight of europium. The glycerin complex is prepared as described in example 1A. 3.65 g of complex are obtained.

The glycerin complex is hydrolysed in a Soxhlet apparatus during 8 days. After drying at 110° C. during 12 hours, the magnetic oxide has the following properties: HC = 151 Oe and $\sigma$ s = 66.

B. The magnetic oxide containing 0.5% of europium, obtained as described in example 4A, is annealed at 350° C. during 1 hour, under a nitrogen stream of 0.5 liter/minute. The annealed product has a Hc of 206 Oe and a $\sigma$ s of 74.36.

Following table VII shows the magnetic properties of the oxides obtained in examples 4A and 4B.

TABLE VII

| Example | Hc | Br | Bs | $\sigma$ s |
|---|---|---|---|---|
| 4A | 151 | 1393 | 3600 | 66 |
| 4B | 206 | 1615 | 3940 | 74,36 |

EXAMPLE 5

A. 20 g of iron (II) oxalate, 0.852 g of cobalt nitrate and 47.56 mg of europium nitrate are dispersed in anhydrous glycerin.

The glycerin complex is prepared in the manner described in example 3A. After washing and drying, 14.66 g of complex containing 2.14% of cobalt and 0.1312% of europium are obtained.

When this glycerin complex is hydrolysed during 2 hours, a magnetic oxide containing 2.13% of cobalt and 0.12% of europium is obtained.

B. By annealing the hydrolysed glycerin complex obtained in example 5A, under a stream of nitrogen, during 1 hour, one obtains a magnetic oxide containing 2.13% of cobalt and 0.11% of europium.

C. When the glycerin complex obtained in example 5A is hydrolysed in a Soxhlet apparatus, the obtained oxide contains 2.13% of cobalt and 0.052% of europium.

D. After thermal annealing of the oxide obtained in example 5C, the oxide contains 2.12% of cobalt and 0.052% of europium.

Following table VIII shows the magnetic data of the oxides obtained in examples 5A, 5B, 5C and 5D.

TABLE VIII

| Example | Hc | Br | Bs | $\sigma$ s |
|---|---|---|---|---|
| 5A | 365 | 1897 | 3547 | 71 |
| 5B | 506 | 2326 | 3806 | 73 |
| 5C | 531 | 2180 | 3737 | 72 |
| 5D | 556 | 1942 | 2900 | 73 |

This table shows the beneficial effects of the treatments according to this invention, i.e. the thermal annealing under nitrogen of an oxide obtained by hydrolysis (example 5B), the hydrolysis in a Soxhlet apparatus of the glycerin complex (example 5C) and the thermal annealing under nitrogen of the glycerin complex hydrolysed in a Soxhlet apparatus (example 5D), in comparison with the properties of the oxide (example 5A) obtained without using one of said treatments.

EXAMPLE 6

A. 20 g of iron (II) oxalate, 0.8295 g of cobalt nitrate and 0.828 g of yttrium nitrate are mixed, the obtained mixture containing 2.5% of cobalt and 2% of yttrium.

The glycerin complex is prepared in the manner described in example 3A (15.67 g).

The glycerin complex is hydrolysed during 24 hours in a Soxhlet apparatus and after drying during 12 hours, the magnetic data of the obtained oxide are as follows: Hc = 160 Oe and $\sigma$ s = 57.4.

B. The oxide obtained by hydrolysis in a Soxhlet apparatus as described in example 6A is annealed at 350° C. during 1 hour under a nitrogen stream of 0.5 liter/minute. The magnetic data of the so treated oxide are as follows: Hc = 350 Oe and $\sigma$ s = 64.1.

Table XI shows the magnetic properties of the oxides described in examples 6A and 6B.

TABLE IX

| Example | Hc | Br | Bs | $\sigma$ s |
|---|---|---|---|---|
| 6A | 160 | 1300 | 3000 | 57.4 |
| 6B | 350 | 1800 | 3700 | 64.1 |

EXAMPLE 7

A series of mixed iron and cobalt glycerin complexes are prepared in the manner described in example 3A and are decomposed by hydrolysis in a Soxhlet apparatus as described in example 3C, so as to obtain mixed iron and cobalt oxides containing respectively 2.5% (example 7A), 5% (example 7B) and 10% (example 7C) of cobalt.

Each of the so obtained mixed oxides is then subjected to a thermal annealing during 1 hour at 350° C. under an atmosphere of nitrogen (examples 7D, 7E and 7F).

Following table X shows the magnetic data of the mixed oxides in question, in comparison with those of the monometal oxides of example 1B and example 1C (which only contain $\gamma$-$Fe_2O_3$).

TABLE X

| Example | Hc | Br | Bs | $\sigma$ s |
|---|---|---|---|---|
| 1B | 104 | 1000 | 2700 | 58.2 |
| 7A | 522 | 2080 | 4000 | 73 |
| 7B | 825 | 2200 | 4000 | 75 |
| 7C | 650 | 1577 | 3300 | 59 |
| 1C | 225 | 1232 | 3500 | 72.7 |
| 7D | 850 | 2200 | 4000 | 76 |
| 7E | 1150 | 2300 | 3550 | 70 |
| 7F | 1625 | 2002 | 3628 | 67.11 |

EXAMPLE 8

A series of mixed iron, cobalt and yttrium glycerin complexes are prepared in the manner described in example 3A, and the obtained complexes are then hydrolyzed in a Soxhlet apparatus, so as to obtain mixed oxides having the following cobalt and yttrium contents:

Example 8A: 2.5% cobalt; 0.1% yttrium
" 8B: 2.5% cobalt; 1% yttrium
" 8C: 2.5% cobalt; 2% yttrium
" 8D: 5% cobalt; 0.1% yttrium
" 8E: 5% cobalt; 1% yttrium The various oxides of examples 8A to 8D are then annealed during 1 hour at 350° C. under a stream of nitrogen of 0.5 liters/minute. Corresponding annealed mixed oxides are obtained (examples 8F, 8G, 8H and 8I). The cobalt and yttrium contents of the latter oxides are substantially identical to those of the corresponding oxides obtained by hydrolysis as described in examples 8A to 8D.

Following table XI shows the magnetic data of the oxides of examples 8A to 8I compared to those of the oxides of examples 1B, 1C, 7A, 7B, 7C, 7D, 7E and 7F. This table shows the influence of the cobalt in an iron oxide, as well as the effect of a rare earth element (yttrium) on a mixed iron-cobalt oxide.

TABLE XI

| HYDROLYSIS WITHOUT ANNEALING | | | | |
|---|---|---|---|---|
| Example | Hc | Br | Bs | $\sigma$ s |
| 1B | 104 | 1000 | 2700 | 58.2 |
| 7A | 522 | 2080 | 4000 | 73 |
| 8A | 425 | 1910 | 3460 | 70 |
| 8B | 425 | 2100 | 3600 | 65.8 |
| 8C | 160 | 1300 | 3000 | 57.4 |
| 7B | 825 | 2200 | 4000 | 75 |
| 8D | 650 | 2350 | 4000 | 71.2 |
| 8E | 525 | 1840 | 3300 | 61.8 |
| 7C | 650 | 1577 | 3300 | 59 |
| ANNEALING UNDER NITROGEN AFTER HYDROLYSIS | | | | |
| Example | Hc | Br | Bs | $\sigma$ s |
| 1C | 225 | 1232 | 3500 | 72.7 |
| 7D | 850 | 2200 | 4000 | 76 |
| 8F | 600 | 2200 | 3500 | 71.09 |
| 8G | 500 | 2200 | 4000 | 71.4 |
| 8H | 350 | 1800 | 3700 | 64.1 |
| 7D | 1150 | 2300 | 3550 | 70 |
| 8I | 925 | 2300 | 3600 | 73.1 |
| 8J | 875 | 2200 | 3200 | 69.8 |
| 7F | 2625 | 2002 | 3628 | 67 |

EXAMPLE 9

An iron glycerin complex containing 44.7% of iron and a cobalt glycerin complex containing 39.25% of cobalt are prepared. 3g of the iron complex are mixed to 0.387 g of cobalt complex in a mortar with balls, so as to obtain a mixture of glycerin complexes containing 10.63% of cobalt.

A. 1.2971 g of the mixture of glycerin complexes are hydrolysed. After drying at 110° C., 0.7788 g of hydrolysed mixed oxide containing 9% of cobalt are obtained. Following table XII shows the magnetic properties of this product (example 9A).

B. The hydrolysed mixed oxide is heated at 350° C. during 1 hour under nitrogen. The obtained product (example 9B) also contains 9% of cobalt and has the magnetic properties also indicated in table XII.

In table XII the magnetic properties of the mixed oxides of examples 9A and 9B are compared to those of the mixed oxides containing about the same cobalt amount (10%) of examples 7C and 7F, the latter oxides having been obtained from mixed glycerin complexes prepared by reacting glycerin with a mixture of an iron salt and of a cobalt salt, whereas the mixed oxides of examples 9A and 9B have been obtained from a physical mixture of an iron glycerin complex and a cobalt glycerin complex. This table XII shows that the mixed oxides obtained by the process according to the invention have a homogeneous composition, i.e. a good cation distribution, compared to that of the mixed oxides obtained from mixtures of monometal glycerin complexes.

TABLE XII

| Example | Hc | Br | Bs | $\sigma$ s |
|---|---|---|---|---|
| 9A | 250 | 1100 | 1800 | 45 |
| 9B | 700 | 1400 | 2400 | 57 |
| 7C | 650 | 1577 | 3300 | 59 |
| 7F | 1625 | 2002 | 3628 | 67.11 |

EXAMPLE 10

A. 17.82 g of ferrous oxalate ($2H_2O$) are mixed with 0.2996 g of zinc nitrate ($6.H_2O$), the obtained mixture having an Fe:Zn atomic composition of 99:1. The mixture of the two salts is dispersed into 350 ml of glycerin (preferably anhydrous) and the dispersion is heated progressively to 240° C. and maintained at this temperature during 6 hours, under continuous agitation. After cooling, the system is centrifuged and the obtained glycerin complex is washed first with distilled water and then with methanol. The solid is dried in a drier at 60° C. during one night and the dried product is then crushed.

13 to 15 g of glycerin complex of iron and zinc are obtained. The X-rays and infrared spectra are identical to those described in example 1A (tables I and II).

About 3 g of said glycerolate are dispersed in 1.8 litres of distilled water and the dispersion is maintained at boiling temperature during 2 hours. After centrifugation, the obtained solid (1.6 to 1.8 grams) is dried at 110° C. during several hours. The so obtained iron and zinc oxide (example 10 A) has a coercitive field of 149 Oe and a magnetization at saturation of 75.4 Oe cm3/gr.

B. 1 g of the oxide obtained by the hydrolysis described in example 10A is annealed for example at 350° C. during 1 hour, under a stream of nitrogen of 0.03 m3/hour. 0.98 gr of magnetic oxide of iron and zinc having the following magnetic data are obtained: Hc = 163 Oe and $\sigma$ s = 80.5 Oe cm3/gr (example 10 B).

EXAMPLES 11 to 14

Mixed iron and zinc oxides containing various amounts of zinc are prepared in the manner described in examples 10 A and 10 B.

The amounts of salts dispersed in 350 ml of glycerin for obtaining the various glycerin complexes are as follows:

| Fe : Zn | Examples | Weight of ferrous oxalate (2H$_2$O) in grams | Weight of zinc nitrate (6 H$_2$O) in grams |
|---|---|---|---|
| 98:2 | 11 | 17.64 | 0.595 |
| 97:3 | 12 | 17.46 | 0.8927 |
| 95:5 | 13 | 17.1 | 1.4875 |
| 90:10 | 14 | 16.21 | 2.9771 |

The magnetic properties of the mixed oxides of iron and zinc of examples 10 to 14, obtained after hydrolysis of the corresponding glycerin complexes (series A) and after annealing of the hydrolysed oxides (series B) are given in following table XIII.

This table shows that the most important effect of the annealing treatment is a significant improvement of the values of the saturation magnetization ($\sigma$ s).

TABLE XIII

| OXIDES AFTER HYDROLYSIS WITHOUT ANNEALING | | | | |
|---|---|---|---|---|
| Example | Hc (Oe) | Br (G) | Bs (G) | $\sigma$ s (Oe cm3/gr) |
| 10A | 149 | 1589 | 4021 | 75.4 |
| 11A | 126 | 1247 | 4248 | 74.9 |
| 12A | 148 | 1719 | 4297 | 79.4 |
| 13A | 134 | 1600 | 4336 | 81.2 |
| 14A | 134 | 1576 | 4504 | 86.8 |
| OXIDES ANNEALED UNDER NITROGEN AFTER HYDROLYSIS | | | | |
| 10B | 163 | 1771 | 4351 | 80.5 |
| 11B | 178 | 1628 | 3765 | 75.5 |
| 12B | 151 | 1864 | 4671 | 84.7 |
| 13B | 186 | 1960 | 4450 | 87.7 |
| 14B | 164 | 1631 | 4350 | 89.2 |

EXAMPLES 15 to 17

A series of iron-cobalt-zinc glycerin complexes are prepared in the manner described in example 10 A, using the suitable amounts of starting salts for obtaining the following atomic ratios of Fe:Co:Zn:98:1:1 (example 15), 97:1:2 (example 16) and 96:1:3 (example 17). For example, for obtaining the atomic ratio of 98:1:1, 17.64 gr of ferrous oxalate (2.H$_2$O), 0.249 gr of cobalt acetate (4 H$_2$O) and 0.297 gr of zinc nitrate (6 H$_2$O) are dispersed in 350 ml of anhydrous glycerin and the glycerin complex is prepared as described in example 10 A.

The amounts of salts used for obtaining the various glycerin complexes are as follows:

| Fe : Co : Zn | Weight of ferrous oxalate (2H$_2$O) in grams | Weight of cobalt acetate (4H$_2$O) in grams | Weight of zinc nitrate (6H$_2$O) in grams |
|---|---|---|---|
| 98:1:1 | 17.64 | 0.249 | 0.297 |
| 97:1:2 | 17.46 | 0.249 | 0.596 |
| 96:1:3 | 17.28 | 0.249 | 0.8925 |

The glycerin complexes are hydrolysed under the conditions described in example 10 A and the properties of the obtained oxides are measured (examples 15 A, 16 A and 17 A).

Each of these oxides is annealed during 1 hour at 350° C. under a stream of nitrogen (examples 15 B, 16 B and 17 B).

Following table XIV shows the magnetic data of said oxides respectively after hydrolysis and after thermal annealing.

TABLE XIV

| OXIDES AFTER HYDROLYSIS AND WITHOUT ANNEALING | | | | |
|---|---|---|---|---|
| Examples | Hc (Oe) | Br (G) | Bs (G) | $\sigma$ s (Oe cm3/gr) |
| 15 A | 215 | 1666 | 3333 | 67 |
| 16 A | 210 | 1452 | 4149 | 76.4 |
| 17 A | 217 | 1696 | 4240 | 80.9 |
| OXIDES ANNEALED UNDER NITROGEN AFTER HYDROLYSIS | | | | |
| 15 B | 412 | 2236 | 5478 | 79.1 |
| 16 B | 221 | 1494 | 6041 | 88.3 |
| 17 B | 250 | 1680 | 5835 | 86.5 |

As shown in this table, the presence of 1% of cobalt causes an increase of the coereitive field, whereas the zinc improves the purity ($\sigma$ s) of the oxides. The annealing causes alarge increase of the induction at saturation (Bs) and of the specific magnetization at saturation ($\sigma$ s).

EXAMPLES 18 TO 20

Another series of magnetic oxides are prepared from triple Fe-Co-Zn glycerin complexes, in which the Fe:Co:Zn atomic compositions are as follows: 97:2:1 (example 18), 96:2:2 (example 19) and 95:2:3 (example 20).

The respective amounts of the starting salts dispersed in 350 ml of glycerin are as follows:

| Fe : Co : Zn | Ferrous oxalate (2H$_2$O) in grams | Cobalt acetate (4H$_2$O) in grams | Zinc nitrate (6H$_2$O) in grams |
|---|---|---|---|
| 97:2:1 | 17.46 | 0.498 | 0.297 |
| 96:2:2 | 17.28 | 0.498 | 0.595 |
| 95:2:3 | 17.10 | 0.498 | 0.8958 |

The glycerin complexes obtained in the manner described in example 10 A are hydrolysed in boiling water during 2 hours, using 3 g of glycerin complex dispersed in 1.8 liters of water. The obtained oxides are dried and the magnetic properties thereof are measured (examples 18 A, 19 A and 20 A).

1 g of each oxide obtained by hydrolysis is annealed during 1 hour at 350° C. under a stream of nitrogen and the magnetic properties of the annealed oxides are measured.

Table XV shows the magnetic properties of the products of examples 18 to 20.

TABLE XV

| OXIDES AFTER HYDROLYSIS WITHOUT ANNEALING | | | | |
|---|---|---|---|---|
| Examples | Hc (Oe) | Br (G) | Bs (G) | $\sigma$ s (Oe cm3/gr) |
| 18 A | 361 | 1973 | 4109 | 76.6 |
| 19 A | 310 | 1893 | 4128 | 76.6 |
| 20 A | 285 | 1797 | 4224 | 82.5 |
| OXIDES ANNEALED UNDER NITROGEN AFTER HYDROLYSIS | | | | |
| 18 B | 387 | 1945 | 5473 | 81.3 |
| 19 B | 375 | 2173 | 5947 | 86.2 |
| 20 B | 381 | 2025 | 5587 | 88.1 |

EXAMPLES 21 to 23

A series of triple Fe-Co-Zn glycerin complexes are prepared by the method described in example 10 A, so as to obtain the following atomic compositions of Fe:Co:Zn; 96:3:1; 95:3:2; 94:3:3.

The following amounts of salts have been used:

| Fe : Co : Zn | Exs. | Ferrous oxalate (2H₂O) in grams | Cobalt acetate (4H₂O) in grams | Zinc nitrate (6H₂O) in grams |
|---|---|---|---|---|
| 96:3:1 | 21 | 17.28 | 0.747 | 0.296 |
| 95:3:2 | 22 | 17.10 | 0.747 | 0.596 |
| 94:3:3: | 23 | 16.92 | 0.747 | 0.8921 |

The glycerin complexes are hydrolysed as described in example 10 A and the magnetic characteristics of the obtained oxides are measured (examples 21 A, 22 A and 23 A).

Each of the three oxides is then annealed at 350° C. during 1 hour under a stream of nitrogen (examples 21 B, 22 B and 23 B).

Following table XVI shows the magnetic properties of the two series of oxides.

TABLE XVI

| OXIDES AFTER HYDROLYSIS PRIOR TO ANNEALING | | | | |
|---|---|---|---|---|
| Examples | Hc(Oe) | Br(G) | Bs(G) | $\sigma$ s (Oe cm3/gr) |
| 21 A | 459 | 2081 | 3865 | 73.9 |
| 22 A | 355 | 1940 | 4144 | 79.9 |
| 23 A | 329 | 1964 | 4121 | 82.1 |
| OXIDES ANNEALED UNDER NITROGEN AFTER HYDROLYSIS | | | | |
| 21 B | 581 | 2517 | 5370 | 81.2 |
| 22 B | 375 | 2138 | 5532 | 89.5 |
| 23 B | 500 | 2429 | 5896 | 82.5 |

EXAMPLES 24 to 26

A series of three Fe-Co-Zn glycerin complexes, in which the atomic ratios Fe:Co:Zn are respectively of 93:5:2, 90:5:5 and 88:10:2 are prepared in the manner described in example 10 A.

Using the same salts as in examples 15 to 17, the following amounts of these salts are used:

| Atomic Compositions | Examples | Ferrous oxalate (2H₂O) in grams | Cobalt acetate (4H₂O) in grams | Zinc nitrate (6H₂O) in grams |
|---|---|---|---|---|
| 93:5:2 | 24 | 16.74 | 1.235 | 0.595 |
| 90:5:5 | 25 | 16.20 | 1.235 | 1.489 |
| 88:10:2 | 26 | 15.84 | 2.489 | 0.595 |

The glycerin complexes are hydrolyzed as described in example 10 A and then annealed at 350° C. during 1 hour under a stream of nitrogen of 0.03 m3/hour.

The following table XVII shows the magnetic properties of the annealed oxides.

TABLE XVII

| OXIDES ANNEALED UNDER NITROGEN AFTER HYDROLYSIS | | | | |
|---|---|---|---|---|
| Examples | Hc(Oe) | Br(G) | Bs(G) | $\sigma$ s (Oe cm3/gr) |
| 24 | 920 | 2010 | 4060 | 80.8 |
| 25 | 430 | 2000 | 5137 | 91.1 |
| 26 | 1200 | 2100 | 3850 | 81.2 |

The examples 15 to 26 show that the beneficial effect of the zinc in the magnetic oxides containing iron and cobalt appears mainly in respect of the induction at saturation (Bs) and in respect of the specific magnetization at saturation ($\sigma$ s), whereas the cobalt improves substantially the coercitive field (Hc) and the remanent induction (Br).

It is thus possible, by changing the respective amounts of cobalt and zinc introduced when the glycerin complex is prepared, to prepare oxides having magnetic properties which are far better than those of magnetic oxides obtained by the known processes.

What we claim is:

1. A process for preparing magnetic oxides comprising the steps of (a) preparing a glycerin complex of iron or, a glycerin mixed complex of iron and up to 50% of at least one other metal selected from the group consisting of nickel, chromium, manganese, cobalt, zinc, strontium, yttrium, ruthenium, rhodium, barium, lanthanum, cerium, praseodymium, neodymium, promethium, samarium, europium, gadolinium, terbium, dysprosium, holmium, erbium, thulium, ytterbium, tungsten and lead by dispersing an iron (II) salt, or an admixture of an iron (II) salt and a salt of one or more of the metals set forth in the above defined group, into an excess of glycerin, progressively heating the resultant mixture up to a temperature of between 110 and 290° C. while stirring for two to twenty hours, cooling the reaction mixture, removing the excess glycerin by washing, and then drying the glycerin complex and (b) decomposing said glycerin complex into the corresponding mono- or polymetal magnetic oxide by hydrolysis in boiling water or in a Soxhlet apparatus followed by annealing the obtained oxide in an atmosphere of an inert gas at a temperature of from about 300° C. to about 500° C., thereby producing mono or polymetal magnetic oxide.

2. A process according to claim 1 in which in step (a) the mixture of glycerin and the iron (II) salt or admixture of iron (II) salt and salt of one or more of the metals set forth in the defined group, is progressively heated up to a temperature of between 160° and 290° C.

3. A process according to claim 1, in which a glycerin mixed complex containing at least one rare earth element is prepared.

4. A process according to claim 3, in which the rare earth element is yttrium.

5. A process according to claim 3, in which the rare earth element is europium.

6. A process according to claim 1, in which nitrogen is used as the inert gas.

7. A process according to claim 1, in which the glycerin complex is hydrolyzed with boiling water.

8. A process according to claim 1, in which the glycerin complex is hydrolyzed in a Soxhlet apparatus.

9. A process according to claim 1, in which said glycerin mixed complex is of iron and at least one other metal selected from the group consisting of nickel, cobalt, chromium, manganese and zinc.

10. A process according to claim 1, in which said glycerin mixed complex is of iron and cobalt.

11. A process according to claim 1, in which said glycerin mixed complex is of iron, cobalt and zinc.

* * * * *